United States Patent [19]

Munk

[11] 3,930,399
[45] Jan. 6, 1976

[54] VISCOSITY DETECTION APPARATUS AND METHOD

[75] Inventor: Miner N. Munk, Walnut Creek, Calif.

[73] Assignee: Varian Associates, Palo Alto, Calif.

[22] Filed: July 22, 1974

[21] Appl. No.: 490,534

[52] U.S. Cl. ................................. 73/55; 73/61.1 C
[51] Int. Cl.² ........................................ G01N 11/00
[58] Field of Search ............ 73/55, 54, 61.1 C, 23.1

[56] References Cited
UNITED STATES PATENTS

| | | | |
|---|---|---|---|
| 3,535,918 | 10/1970 | Munk | 73/61.1 C |
| 3,589,170 | 6/1971 | Praglin et al. | 73/23.1 |
| 3,592,043 | 7/1971 | Munk | 73/23.1 |
| 3,753,369 | 8/1973 | Fowler et al. | 73/54 X |

Primary Examiner—Richard C. Queisser
Assistant Examiner—Joseph W. Roskos
Attorney, Agent, or Firm—Stanley Z. Cole; John J. Morrissey

[57] ABSTRACT

Apparatus and method applicable to liquid chromatography for continuously detecting the viscosity of the effluent from an analysis column of a chromatograph system. The effluent is forced through a tubular path in a flow resistance element, which may contain a packing material to increase the amount of energy dissipated in the flow resistance element. The temperature of the effluent is sensed before and after passage through the path. A signal is generated which is a function of the difference between the value of temperature which is sensed before and after traversal of the effluent through the tubular path. From these measurements, the viscosity of the effluent may be computed as a function of the observed temperature change.

17 Claims, 6 Drawing Figures

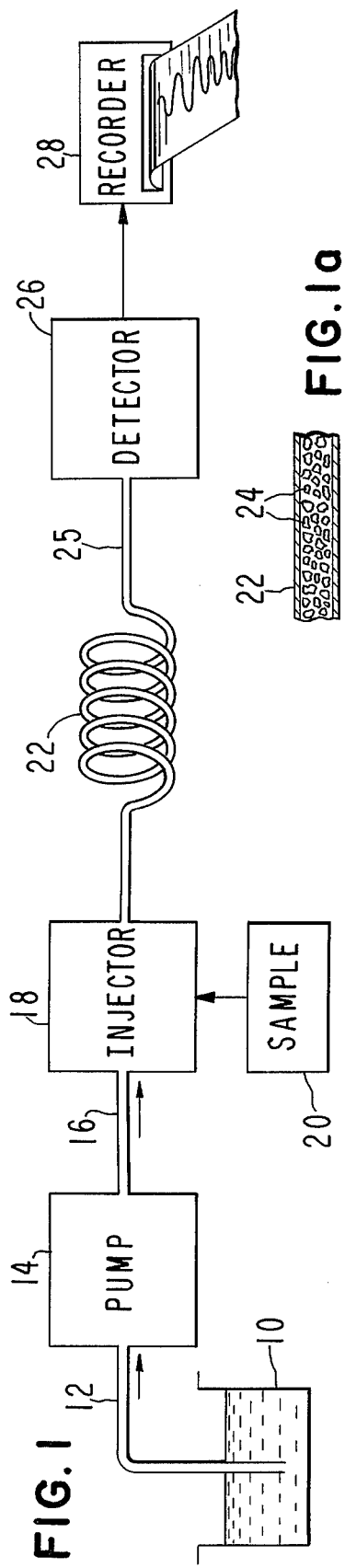
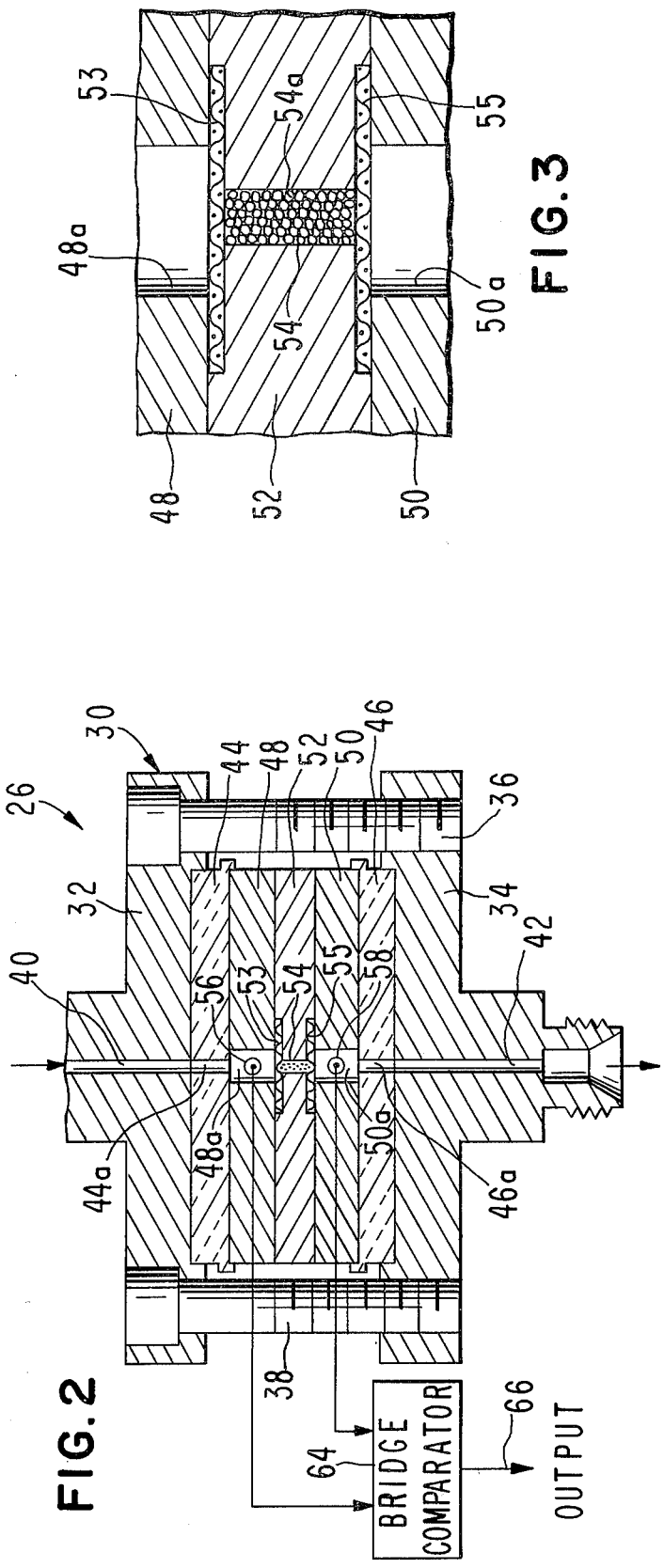

VISCOSITY DETECTION APPARATUS AND METHOD

BACKGROUND OF THE INVENTION

1. Field of the Invention:

This invention relates to the area of liquid chromatography and specifically to continuous detection of viscosity of column effluent in such systems.

2. Description of the Prior Art

Liquid chromatography pertains to a particular variety of equipment and techniques for analyzing the components of an unknown sample of liquid material.

Liquid chromatography is a process wherein a sample having unknown components is forced to migrate through an elongated "column." The column contains a material held statically inside it, called a "stationary phase." The stationary phase is chosen for its ability to selectively retain the various potential components of the sample with which it comes in contact with differing degrees of tenacity. The sample is forced to migrate through the column by injecting it into a solvent upstream of the column and subsequently pumping the solvent and dissolved sample through the column.

When the dissolved sample is forced through the column, each of its components migrates through the column in a particular time related pattern, which pattern is a function of the degree of the tendency of the stationary phase to retain that component.

Some properties of the column effluent are affected by the concentration of sample in the emergent fluid. One of the properties which may be affected is the viscosity of the effluent. By detecting variations in this property of the effluent, and plotting these variations against time, certain information can be derived as to the nature and amount of the components in the sample.

For example, for predetermined column conditions and flow rate, it may be known that a particular hypothetical component, if present in the sample, will reach a maximum concentration in the column effluent at a specific time following introduction of the sample to the column. This time is known as the "retention time" of the component. This phenomenon occurs because of the existence of the particular degree of retention of that component by the stationary phase. By measuring a property of the effluent known to be affected by the hypothetical component, and observing whether a maximum occurs at the "retention time" for that component, presence of the component can be verified or negated.

It is evident that in liquid chromatography there exists a necessity for accurately detecting and measuring, on a continuous basis, properties of the liquid emerging from the column, such as viscosity.

It is known in liquid chromatography to measure many properties of the column effluent to derive information relating to the nature and quantity of the components in a sample. Among the properties measured are visible light and ultraviolet ray absorption, refractive index, heat of absorption and flame ionization of the sample.

SUMMARY OF THE INVENTION

In contrast to the prior art, applicant has invented a new method and apparatus for detecting sample concentration by measuring the viscosity of the effluent stream from the column.

This invention provides a new and improved method and apparatus for continuously detecting the viscosity of a stream of liquid emanating from the column of a liquid chromatograph.

An inlet conduit delivers effluent from the column to a flow resistance element, which comprises the detection structure of the chromatograph system. The flow resistance element defines a tubular path through which the effluent is forced. The liquid incurs a pressure drop in traversing the path, and is frictionally heated as well. A reference temperature sensor produces a signal as a function of the temperature of the entering effluent. A detection sensor produces a signal as a function of effluent temperature after traversal of the flow path. These two temperature signals are compared in a comparator which generates an output signal which is a function of their difference.

BRIEF DESCRIPTION OF THE DRAWINGS

FIG. 1 is a block diagram of a liquid chromatographic system to which the present invention is applicable;

FIG. 1a is a detailed drawing of the column in cross section;

FIG. 2 is a cross-sectional side view of an apparatus embodying the present invention;

FIG. 3 is a detailed sectional drawing of the flow resistance element of said apparatus;

DESCRIPTION OF THE PREFERRED EMBODIMENT

Figure 4:
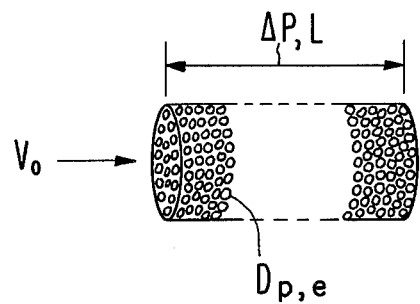
FIG. 4 is a detailed drawing of the tubular path defined by the flow resistance element.

FIG. 1 shows a typical liquid chromatograph system to which the present invention is applicable. A solvent reservoir 10 contains a quantity of solvent, which is drawn along a conduit 12 by a pump 14, and subsequently transported through a conduit 16 to an injector 18. A quantity of sample from a sample reservoir 20 is injected into the solvent by the injector 18. The solvent/sample solution continues on to a column 22. The column 22 is an elongated conduit containing a stationary phase 24 which is shown in FIG. 1a as a solid particulate material.

Components of the sample are selectively retained in the column 22 by the stationary phase 24, emerging in the column effluent at an end 25 of the column 22 in particular time-related patterns. The presence and concentration of these components in the effluent are sensed by a detector 26. The detector 26 generates a signal as a function of the concentration of the component detected, which signal is directed to a recorder 28. The recorder 28 produces a tangible record of the detected concentration of the sample components with respect to time.

FIG. 2 shows a side sectional view of an apparatus embodying the present invention, and which comprises detector 26. A shell, generally indicated at 30, is provided for housing the structure of this preferred embodiment. The shell 30 includes a pair of oppositely facing shell plates 32 and 34. The shell plates 32 and 34 are made of a rigid material. It is also desirable that the shell plates 32 and 34 be made of a material which is chemically inert to the effluent whose viscosity is to be tested. The shell plates 32 and 34 are held together in a rigid configuration by means of bolts 36 and 38. The shell plate 32 is of disc-shaped configuration, and has an inlet conduit 40 centrally disposed therein. The shell plate 34 is also disc-shaped and has an outlet conduit 42 through its center. The inlet conduit 40 is connected to the end 25 of the column, in order to receive the effluent. The outlet conduit 42 carries the effluent which exits the detector, which fluid can either be discarded or collected, as the particular circumstances of use of the invention may dictate.

Two thermal insulating discs 44 and 46 are positioned adjacent the interior surfaces of shell plates 32 and 34, respectively. The insulating disc 44 has a central orifice 44a which communicates with the inlet conduit 40. Similarly, the insulating disc 46 has an orifice 46a communicating with the outlet conduit 42.

A pair of retainer discs 48 and 50 are positioned adjacent the insulating discs 44 and 46 respectively.

A reference sensor 56 is centrally disposed in an opening 48a in the retainer disc 48. A detection sensor 58 is similarly centrally disposed in an opening 50a in retainer disc 50. Each of the sensors 56 and 58 are thermistors in the preferred embodiment. A thermistor is a semiconductor element having a resistance which varies substantially with changes in temperature. The coefficient of resistivity in the thermistor is generally quite large and negative. That is to say, the resistance drops substantially with increases in temperature.

A flow resistance element 52 is disposed between the retainer discs 48 and 50. The flow resistance element 52 defines a tubular flow path 54 in its center. The flow path 54 is covered on either end by screens 53 and 55. The flow path 54 is filled with a fine particulate material, indicated as 54a in FIG. 3.

The inlet and outlet conduits 40 and 42, the orifices 44a and 46a, and the openings 48a and 50a are all aligned to cooperate with the flow path 54 to form a channel through which liquid can flow.

Applicant has determined that the dimensions for the flow path 54 in the preferred embodiment are approximately one-eighth inch in length and .03 inch in diameter. The packing material consists of 29 micron diameter spherical glass beads. The glass beads are retained within the flow path 54 by 10 micron hole diameter screens 53 and 55 at each end of the flow path 54.

Each of the sensors 56 and 58 is electrically connected to an electrical comparator bridge 64. The comparator bridge 64 produces an electrical output signal at an output 66, which output signal is a function of the difference between the resistances of each of the sensors 56 and 58.

The operation of this embodiment of the invention is described as follows. The inlet conduit 40 is connected to the end 25 of the analysis column 22, so that it receives the effluent from the column. The effluent passes through orifice 44a and continues through opening 48a around the reference sensor 56. The reference sensor 56, in response to the temperature of the effluent liquid in contact with it, assumes a particular value of resistance.

The effluent then passes through the flow path 54 in the flow resistance element 52. The screens 53 and 55 permit the passage of the effluent liquid through the flow path 54, while preventing the escape from the flow path of the particulate packing material 54a. During the passage of the effluent liquid through the flow path 54 containing the packing material 54a, energy is dissipated in the effluent. This energy causes an increase in the temperature of the liquid passing through the flow path 54. The effluent, upon emerging from the lower end of the flow path 54, comes in contact with the detection sensor 58. The detection sensor 58 assumes a particular resistance, the value of which is a function of the temperature of the liquid emerging from the flow path 54. The effluent liquid then passes through the orifice 46a and the outlet conduit 42, from which it may be discarded or collected as desired.

Each of the thermistors comprising the reference sensor 56 and the detection sensor 58 is connected to the bridge comparator 64, which consists of an electrical bridge circuit in the preferred embodiment. Bridge circuits are known in the art which are capable of comparing relative resistances with extreme precision. The choice of such a bridge is within the skill of one ordinarily skilled in the relevant art.

The signal output from the bridge comparator 64 appearing at the output 66 is thus a function of the difference in resistances between the thermistors comprising the reference sensor 56 and the detection sensor 58. Consequently, the signal at the output 66 is also a function of the difference in temperature of the effluent liquid immediately before and immediately after the passage through the flow path 54.

It is mathematically demonstrable that the temperature change in liquid flowing across a constriction is a function of the viscosity of that liquid.

The kinetic theory of gases gives the following expression for an ideal gas:

$$\mu = k/C_v$$

where $\mu$ is the coefficient of viscosity, $k$ is the thermal conductivity of the gas, and $C_v$ is the heat capacity of gas at constant volume.

The viscosity of the liquid is representable by the following expression:

$$\mu = A\, e^{-\Delta E_{vis}/RT}$$

where A is a constant, $\Delta E_{vis}$ is the measure of the energy barrier that must be overcome before the elementary flow process can occur, R is the ideal gas constant, and T is the absolute temperature in degrees Kelvin. $\Delta E_{vis}$ will depend on the composition of the fluid.

Considering flow through a long, relatively narrow tube having circular cross section, the pressure drop per unit length is related to the coefficient of viscosity by the "Hagen-Poiseuille law" as follows:

$$\dot{V} = \frac{\Delta P}{L}\, \frac{\pi R^4}{8\mu}$$

where V is the volume flow rate of liquid, $\Delta P/L$ is the pressure drop per unit length of the channel, and R is the radius of the circular channel. Other channel cross sections can be accounted for by using the hydraulic radius in this equation. The pressure drop is thus directly proportional to the coefficient of viscosity $\mu$.

When considering a relatively short flow path containing packing material, as indicated in FIG. 4, the pressure drop per unit length is related to the coefficient of viscosity, $\mu$, by the following "Blake-Kozeny equation" for laminar flow:

$$v_o = \frac{\Delta P}{L}\, \frac{D_p^2}{150\mu}\, \frac{e^3}{(1-e)^2}$$

where $v_o$ is the superficial velocity (the velocity that liquid would have in the absence of packing material for the particular flow rate), $D_p$ is the particle diameter of the packing material (provided the particles are spherical), and $e$ is the void volume of the flow path relative to the total volume of the flow path. Rearrangement of the above equation results in the following expression:

$$\Delta P/L = B\mu$$

where $B$ is a constant for the system if the flow rate is maintained constant. In this situation, as well as in the previously described situation, the pressure drop is directly proportional to the viscosity of the liquid flowing through the flow path.

When a liquid flows through a packed flow path, the amount of heat generated by that flow path, and consequently the increase in temperature of the liquid passing through the flow path, is a function of the viscosity of the liquid. The reason for this is that more energy is dissipated with the passage of a fluid of greater viscosity through such a column than with the passage of a fluid with lesser viscosity.

Figure 5:
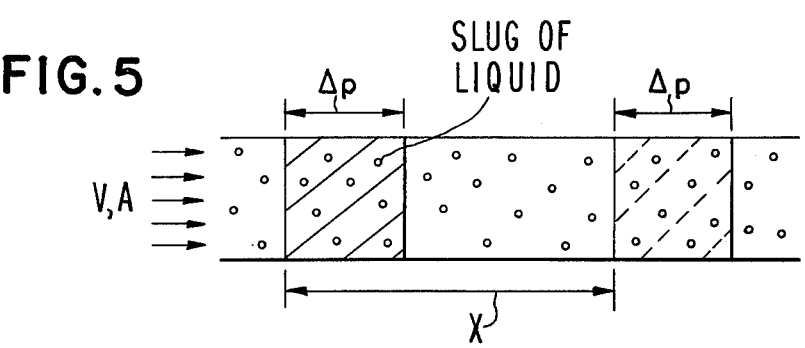
FIG. 5 is a detailed drawing showing the transport phenomenon occurring with the passage of liquid through the tubular path.

FIG. 5 shows a longitudinal section sketch of a flow path. In a certain length of time, a slug of liquid in a flow path can be forced to move a distance x. The force acting on this slug is the pressure drop from the upstream face of the slug to the downstream face, that is, $$F = \Delta p \cdot A$$

where $A$ is the area of the cross section of the slug of liquid. If one assumes a steady state condition, this force must be balanced by frictional forces as the portion of liquid is moved along. The work done against the frictional forces is the force times the distance, or $$W = F \cdot x = \Delta p \cdot A \cdot x$$

The time, $t$, in which this work is done is the volume swept out by the slug of liquid divided by the volume flow rate of the liquid. This time is expressable as:

$$t = (x \cdot A)/\dot{V}$$

where $\dot{V}$ is the volume flow rate of the liquid. The work per unit time is the power dissipated in the liquid. Thus:

power dissipated =

$$W/t = \frac{p \, \Delta P \cdot A \cdot x}{(x \cdot A)/(\dot{V})}$$

power dissipated = $\Delta P \cdot \dot{V}$

If one assumes that the flow path is very well insulated thermally so that no heat is lost from it, the power dissipated all goes into heating the liquid flowing through the flow path. (In actual practice, there will be a short lived transient in the temperature rise of the fluid moving through the flow path due to the heat capacity of the packing material within the flow path. This transient is relatively short, however, and need not be considered.) Thus, the temperature rise in the liquid is the power dissipated into it divided by the product of its heat capacity and the volume flow rate of liquid through the flow path. Thus:

$$\Delta T = \text{temperature rise of liquid} = \frac{\text{power dissipated}}{\rho \cdot C \cdot \dot{V}}$$

$$= \frac{\Delta p \cdot \dot{V}}{\rho \cdot C \cdot \dot{V}}$$

$$\Delta T = \frac{\Delta P}{\rho C}$$

where $\rho$ is the density of the liquid and $C$ is the heat capacity per unit mass of the liquid. Since the pressure drop is proportional to the viscosity of the liquid, the following expression for the temperature rise of the liquid holds true:

$$\Delta T = \frac{k \mu}{\rho c}$$

where $k$ is a constant for a constant flow rate of liquid through the flow path.

The disclosure of this application is intended to be illustrative, rather than exhaustive. Persons of ordinary skill in the relevant art, when aided by this disclosure, will be able to make changes and modifications in the embodiments disclosed herein without departing from the spirit of this invention.

What is claimed is:

1. Apparatus for measuring the viscosity of effluent from the column of a liquid chromatograph, said apparatus comprising:
    a. a flow resistance element having an elongated flow path therethrough, said flow path having an entrance and an exit connectable to carry a flow of effluent from the column through said flow path, said flow path containing packing material;
    b. a reference sensor disposed outside said flow resistance element to sense the temperature of the effluent entering said flow resistance element; and
    c. a detection sensor disposed outside said flow resistance element to sense the temperature of the effluent exiting from the flow resistance element.
2. The apparatus of claim 1, wherein:
said reference sensor comprises a thermistor disposed proximate to said entrance.
3. The apparatus of claim 1, wherein:
said detection sensor comprises a thermistor disposed proximate to said exit.
4. The apparatus of claim 1, further comprising:
a comparator connected to each of said reference and said detection sensors for producing a differential signal which is a function of the difference between the temperatures sensed by said reference and detection sensors.
5. The apparatus of claim 4, wherein:
said comparator comprises an electrical bridge circuit.
6. The apparatus of claim 1, wherein:
said flow path has a tubular configuration.
7. The apparatus of claim 1, wherein:
said packing material is particulate.
8. The apparatus of claim 7, wherein:
said packing material comprises spherical glass beads.
9. The apparatus of claim 7, further comprising:
a screen interposed across each of said entrance and exit of said flow path for retaining said packing material within said flow path.
10. The apparatus of claim 1, further comprising:
a housing enclosing said flow resistance element, and each of said reference and said detection sensors.
11. The apparatus of claim 10, further comprising:
thermal insulation disposed within said housing to insulate said flow resistance element and said sensors from thermal exchange with the environment external to said housing.
12. The apparatus of claim 11, wherein:

said flow resistance element comprises a first disc mounted within said housing and having an aperture through its center, said aperture comprising said flow path.

13. The apparatus of claim 12, further comprising:
a. a retainer disc mounted within said housing adjacent one side of said first disc and disposed for supporting said reference sensor, and
b. another retainer disc mounted within said housing adjacent the other side of said first disc and disposed for supporting said detection sensor.

14. A method for measuring the viscosity of effluent from the column of a liquid chromatograph utilizing known properties of said effluent and known operating parameters of said chromatograph, said method comprising the steps of:
a. forcing the effluent through an elongated flow path having an entrance and exit;
b. sensing the temperature of the effluent entering said flow path;
c. sensing the temperature of the effluent exiting from the flow path;
d. comparing the sensed entrance and exit temperatures, and
e. deriving an indication of the viscosity of said effluent from the comparison of said sensed entrance and exit temperatures and from said known properties of said effluent and said known operating parameters of said chromatograph.

15. The method of claim 14, further comprising the step of:
rendering said flow path tortuous to the passage of liquid therethrough.

16. The method of claim 14, further comprising the step of:
retarding heat exchange between the region of said flow path and the environment external to said flow path.

17. A method for identifying components of a liquid sample, said method comprising the steps of:
a. passing the sample through a column of a liquid chromatograph having known operating parameters, and
b. detecting the viscosity of the effluent of the column utilizing known properties of said effluent and the known operating parameters of said chromatograph by
  i. forcing the effluent through an elongated flow path having an entrance and exit;
  ii. sensing the temperature of the effluent entering said flow path;
  iii. sensing the temperature of the effluent exiting from the flow path; and
  iv. comparing the sensed entrance and exit temperatures.

* * * * *